(12) United States Patent
Luo et al.

(10) Patent No.: US 9,360,401 B2
(45) Date of Patent: Jun. 7, 2016

(54) SAMPLE STACK STRUCTURE AND METHOD FOR PREPARING THE SAME

(71) Applicant: INOTERA MEMORIES, INC., Taoyuan (TW)

(72) Inventors: Jian-Shing Luo, Taoyuan County (TW); Hsiu-Ting Lee, Kaohsiung (TW)

(73) Assignee: INOTERA MEMORIES, INC., Hwa-Ya Technology Park Kueishan, Taoyuan (TW)

( * ) Notice: Subject to any disclaimer, the term of this patent is extended or adjusted under 35 U.S.C. 154(b) by 0 days.

(21) Appl. No.: 14/495,864

(22) Filed: Sep. 24, 2014

(65) Prior Publication Data

US 2016/0084742 A1    Mar. 24, 2016

(51) Int. Cl.
| | |
|---|---|
| H01L 21/00 | (2006.01) |
| G01N 1/28 | (2006.01) |
| H01J 37/26 | (2006.01) |
| H01J 37/305 | (2006.01) |
| H01L 21/78 | (2006.01) |
| H01L 21/48 | (2006.01) |
| H01L 23/522 | (2006.01) |
| H01L 23/00 | (2006.01) |

(52) U.S. Cl.
CPC ............... *G01N 1/286* (2013.01); *H01J 37/261* (2013.01); *H01J 37/3056* (2013.01); *H01L 21/486* (2013.01); *H01L 21/4814* (2013.01); *H01L 21/78* (2013.01); *H01L 23/5226* (2013.01); *H01L 24/01* (2013.01); *G01N 2001/2886* (2013.01); *H01J 2237/31745* (2013.01)

(58) Field of Classification Search
CPC ......... G01N 1/28; G01N 1/2806; G01N 1/32; H01J 2237/31745
See application file for complete search history.

(56) References Cited

U.S. PATENT DOCUMENTS

| | | | | | |
|---|---|---|---|---|---|
| 5,993,291 | A | * | 11/1999 | Tsai | B24B 49/00 451/28 |
| 7,649,173 | B2 | * | 1/2010 | Hu | G01N 1/32 216/33 |
| 8,481,968 | B2 | * | 7/2013 | Luo | G01N 1/286 250/307 |
| 8,513,620 | B2 | * | 8/2013 | Huang | H01J 37/20 250/310 |
| 2004/0164242 | A1 | * | 8/2004 | Grunewald | G01N 1/32 250/307 |
| 2010/0308219 | A1 | | 12/2010 | Blackwood | |
| 2012/0273692 | A1 | | 11/2012 | Tokuda | |
| 2013/0209700 | A1 | | 8/2013 | Suzuki | |
| 2013/0209701 | A1 | | 8/2013 | Suzuki | |

* cited by examiner

*Primary Examiner* — Reema Patel
*Assistant Examiner* — Syed Gheyas
(74) *Attorney, Agent, or Firm* — Winston Hsu; Scott Margo

(57) ABSTRACT

The present invention provides a sample stack structure with multiple layers. The sample stack structure has at least a substrate, an adhesive layer and a target layer. The target layer is directly sandwiched between the substrate and the adhesive layer.

10 Claims, 17 Drawing Sheets

SAMPLE STACK STRUCTURE AND METHOD FOR PREPARING THE SAME

BACKGROUND OF THE INVENTION

1. Field of the Invention

The present invention generally relates to a method for preparing a sample stack structure and a sample stack structure. In particular, the present invention is directed to a method for preparing a sample stack structure by a combination of backside milling and dicing and a sample stack structure prepared by the method so as to be free from a curtain effect. The sample stack structure has a target layer which is attached to a dummy substrate part by an adhesive layer.

2. Description of the Prior Art

A transmission electron microscopy (TEM) plays an important role in the structural analysis and characterization of materials for process evaluation and failure analysis in the integrated circuit (IC) industry as the device shrinkage continues. It is well known that a high quality TEM sample is one of the key factors which enable to facilitate successful TEM analysis. Various cross-sectional TEM (XTEM) sample preparation techniques have been reported for these purposes.

These proposed techniques are generally categorized as below:
(1) dimpling or mechanical polishing and $Ar^+$ ion milling;
(2) mechanical polishing and focused ion beam (FIB) milling;
(3) FIB milling and ex-situ lift-out;
(4) in-situ lift-out and FIB milling; or
(5) dicing saw and FIB milling.

The FIB milling has become a favorable choice as it offers several indispensable advantages compared to conventional mechanical techniques. For example, FIB milling allows a uniform thinning of complex heterogeneous structures with different sputtering rates and provides the capability and precision in localizing the specific regions of interest that is essential for site specific defect analysis. In addition, a dicing saw provides a good method to prepare TEM pre-thin samples with high efficiency.

In particular, a disadvantage called curtain effect, which causes uneven and damaged surfaces, is a well-known issue to TEM sample preparation. It becomes more serious with device size shrinking and low voltage milling utilization. Some adverse examples are given in FIG. 1, FIG. 2 and FIG. 3. FIG. 1 shows a TEM image in which the curtain effect (lighter and darker parallel patterns) damages the structures from top layer to Si-substrate. FIG. 2 shows another TEM image in which the curtain effect (lighter and darker parallel patterns) is observed, too. FIG. 3 shows a silicon map in which the sample surface is damaged and the damaged surface influences the analysis result of silicon elemental distribution mapping.

Given the above, a disadvantageous curtain effect results in poor quality of TEM analysis. A few methods were suggested to reduce the curtain effect, such as tilting the sample, polishing/dipping in acid to remove top layers or backside milling.

However, sample tilting cannot eliminate the curtain effect completely. For backside polishing, it can eliminate the curtain effect completely, but the thickness of the sample needs reducing in a first place, which is quite time consuming and needs more works for specific location analysis. As to polishing/dipping in acid to remove top layers, it is quite dangerous and complex.

SUMMARY OF THE INVENTION

In the light of the above, the present invention proposes a method for preparing a sample stack structure and a sample stack structure prepared by the method. This novel method is capable of eliminating the curtain effect completely with high efficiency by a combination of backside milling and dicing so the sample stack structure has a special stack structure which is free from a curtain effect under observation for later structural analysis and characterization of materials. The sample stack structure may also have an optimal thickness.

The present invention in a first aspect provides a method for preparing a sample stack structure. First, a chip set which includes at least two chips with a substrate and a target layer is provided. Second, cutting the chip set several times to form a sample dice and a dummy dice. Each sample dice and dummy dice has a shoulder portion and a bottom portion. The shoulder portion has the substrate and the target layer. Then, the target layer of the sample dice is attached to the substrate of the dummy dice by an adhesive layer. Next, the bottom portion of the sample dice is removed so that the target layer and some of the substrate of the sample dice are attached to the dummy dice by the adhesive layer to obtain a sample stack structure.

In one embodiment of the present invention, the chip set includes a first dice and a second dice so that the first dice is the sample dice and the second dice is the dummy dice.

In another embodiment of the present invention, the adhesive layer includes an epoxy resin.

In another embodiment of the present invention, the target layer has a composite material including a semicinductive material.

In another embodiment of the present invention, the shoulder portion of the sample dice is attached to the bottom portion of the dummy dice by the adhesive layer.

In another embodiment of the present invention, the method for preparing a sample stack structure further includes to form a metal pad on the substrate of the sample dice after removing the bottom portion of the sample dice.

In another embodiment of the present invention, the method for preparing a sample stack structure further includes to form a first trench penetrating the substrate, the adhesive layer and the target layer which is sandwiched between the substrate and the adhesive layer.

In another embodiment of the present invention, the method for preparing a sample stack structure further includes to form a first via connecting the first trench and penetrating the substrate, the adhesive layer and the target layer which is sandwiched between the substrate and the adhesive layer.

In another embodiment of the present invention, the method for preparing a sample stack structure further includes to form a second trench penetrating the substrate, the adhesive layer and the target layer which is sandwiched between the substrate and the adhesive layer. The second trench and the first trench are disposed on two opposite sides of the sample dice.

In another embodiment of the present invention, the method for preparing a sample stack structure further includes to form a second via connecting the second trench and penetrating the substrate, the adhesive layer and the target layer which is sandwiched between the substrate and the adhesive layer.

The present invention in a second aspect provides a sample stack structure with multiple layers. The sample stack structure has at least a substrate, an adhesive layer and a target layer. The target layer is directly sandwiched between the substrate and the adhesive layer. In one embodiment of the present invention, the smallest dimension of the sample stack structure is not greater than 4000 Å.

In another embodiment of the present invention, the substrate is a semicinductive material.

In another embodiment of the present invention, the target layer has a composite material including the semicinductive material.

In another embodiment of the present invention, the adhesive layer comprises an epoxy resin.

In another embodiment of the present invention, the sample stack structure further includes a dummy layer attached to the adhesive layer.

In another embodiment of the present invention, the sample stack structure further includes a metal pad which partially covers a surface of the substrate.

In another embodiment of the present invention, the sample stack structure further includes a first trench which penetrates the substrate, the target layer and the adhesive layer.

In another embodiment of the present invention, the sample stack structure further includes a first via which connects the first trench and penetrates the substrate, the target layer and the adhesive layer.

In another embodiment of the present invention, the sample stack structure further includes a second trench penetrates the substrate, the target layer and the adhesive layer. The second trench and the first trench are disposed on two opposite sides of the sample stack structure.

In another embodiment of the present invention, the sample stack structure further includes a second via connects the second trench and penetrates the substrate, the target layer and the adhesive layer.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 7 illustrates a top view of the chips in the chip set arranged and fixed on the platform and FIG. 7A illustrates a side view of the chips in the chip set arranged and fixed on the platform.

FIG. 8 illustrates a top view of the chip set arranged and fixed on the platform and FIG. 8A illustrates a side view of the chip set arranged and fixed on the platform.

FIG. 10 illustrates a top view of the chip set arranged and fixed on the platform and FIG. 10A illustrates a side view of the chip set arranged and fixed on the platform.

FIG. 12 illustrates a top view and FIG. 12A illustrates a side view.

FIG. 13 illustrates a top view and FIG. 13A illustrates a side view.

DETAILED DESCRIPTION

The present invention provides a sample stack structure and a method for preparing a sample stack structure. This novel method is capable of eliminating the curtain effect completely with high efficiency by a combination of backside milling and dicing without using sample tilting, backside polishing, or polishing/dipping in acids, so the sample stack structure is free of a curtain effect under observation by a simpler approach.

FIG. 4 to FIG. 13 illustrate a possible way to prepare a sample stack structure of the present invention. In some figures, a top view and a side view may be given collectively for a better illustration purpose. First, please refer to FIG. 4. A wafer 100 is provided. The wafer 100 has various layers of different material, such as oxides, nitrides, metals or semiconductive materials, Si or doped Si for example.

For instance, the wafer 100 has a target layer 111 and a substrate 112. Sometimes, a wafer of various different material layers needs structural analysis and characterization of materials for process evaluation and failure analysis so a sample piece is required to be taken from a wafer. A target layer 111 for analysis or for evaluation is disposed on a substrate 112. However, if the sample piece with the target layer is done in a conventional way, it suffers the curtain effect under the observation of a TEM. One of the features of the method of the present invention resides in dicing and combining a wafer in a special sequence to obtain a sample structure free of curtain effect.

Figure 1:
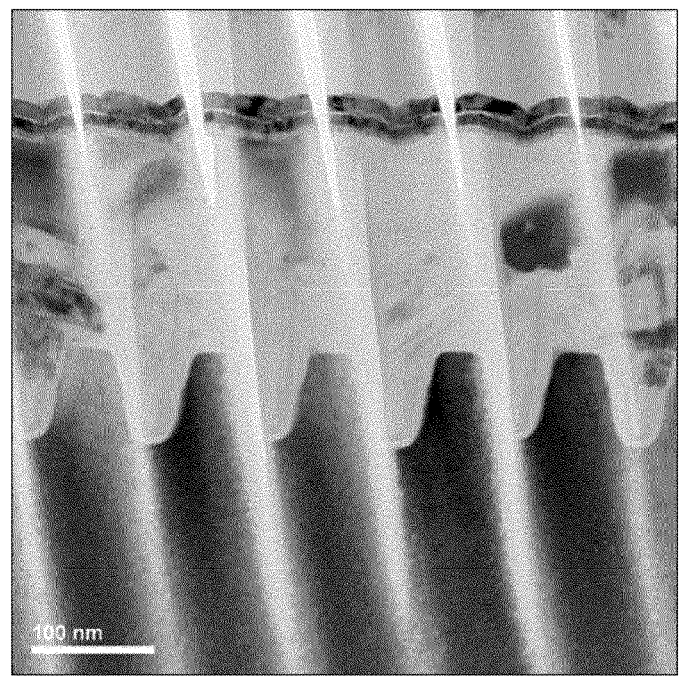
FIG. 1 shows a TEM image in which the curtain effect (lighter and darker parallel patterns) damaged the structures from top layer to Si-substrate in prior art.
Figure 2:
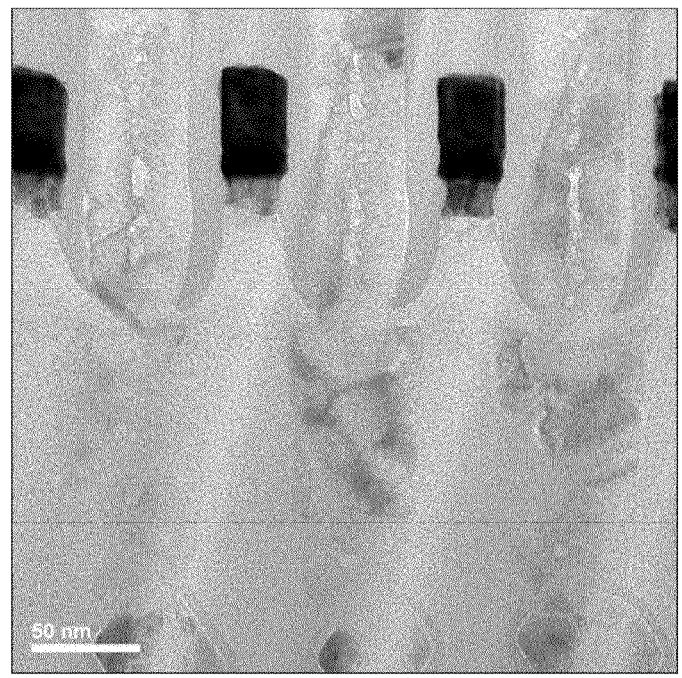
FIG. 2 shows another TEM image in which the curtain effect (lighter and darker parallel patterns) was observed in prior art.
Figure 3:
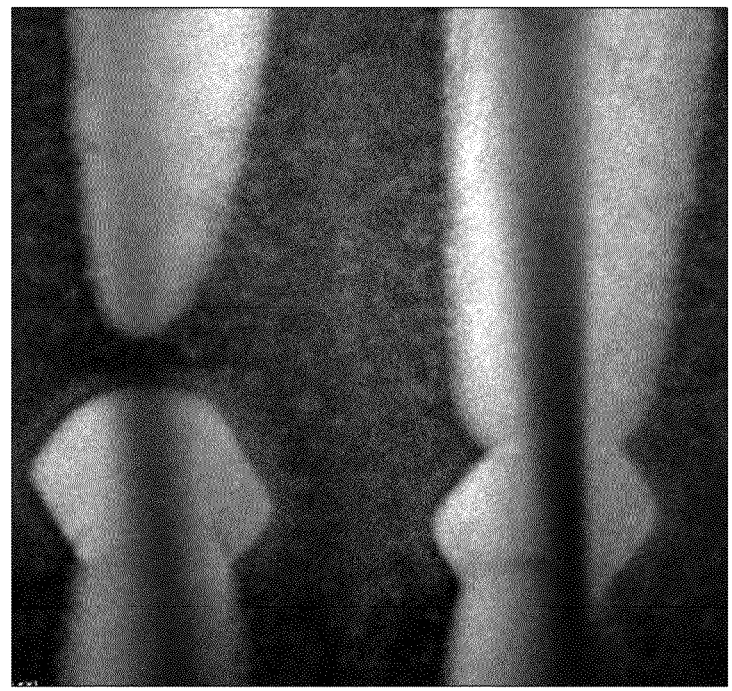
FIG. 3 shows a silicon map in which the sample surface was damaged and the damaged surface influenced the analysis result of silicon elemental distribution mapping in prior art.
Figure 4:
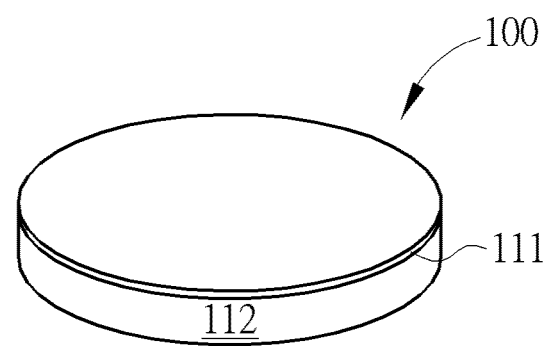
FIG. 4 to FIG. 13 illustrate a possible way to prepare a sample stack structure of the present invention.
Figure 5:
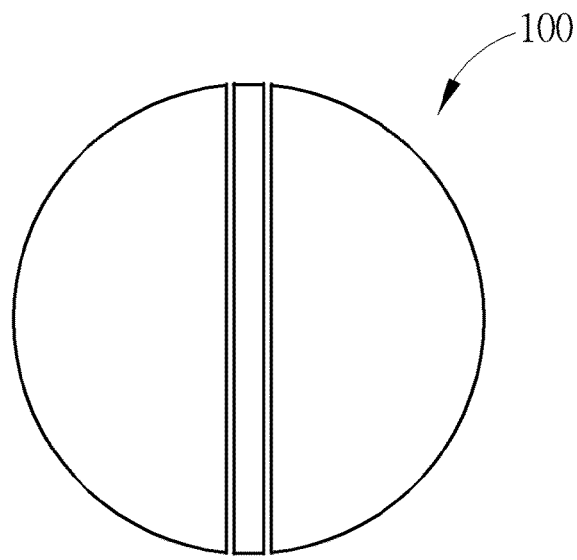
Figure 5A:
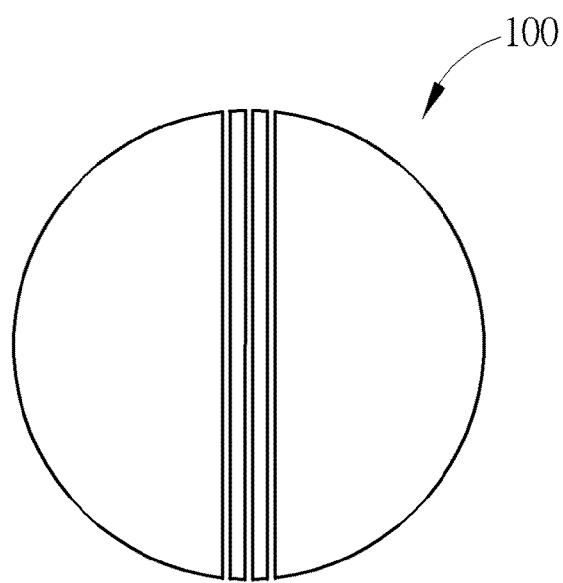
FIG. 5A shows an alternative example of the wafer to be cleaved.
Figure 6:
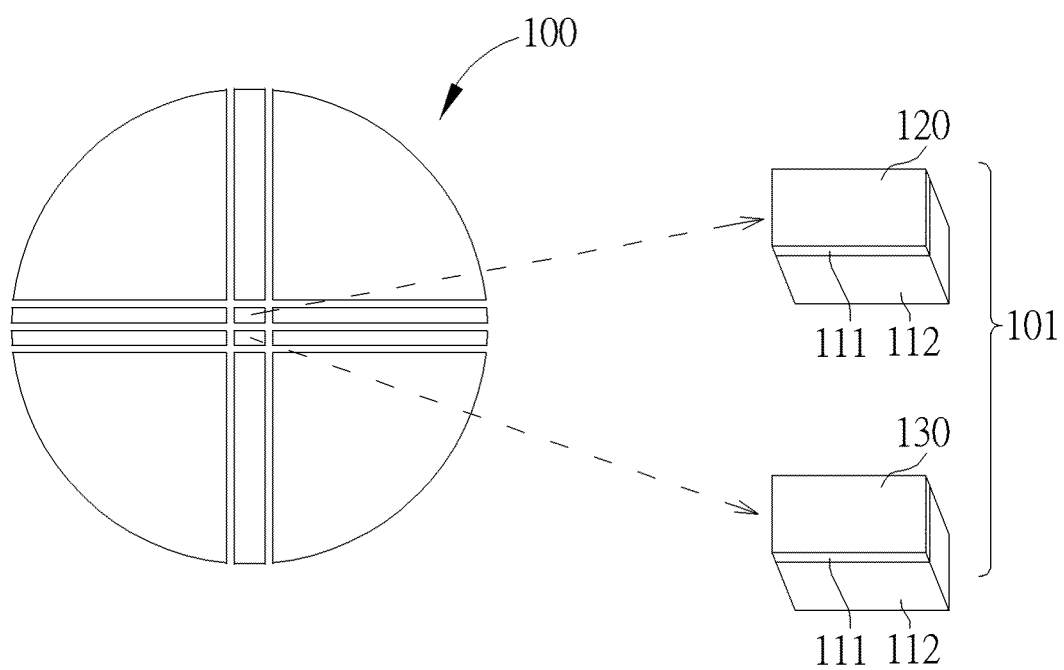

Second, as shown in FIG. 5, FIG. 5A and FIG. 6, the wafer 100 is cleaved to get several chips, one or more chips for example. These chips, two chips 120 and 130 for the purpose of simplicity as shown in FIG. 6, are collectively called a chip set 101 but there may be more than two chips in a chip set 101. Each chip in the chip set 101 includes a target layer 111 and a substrate 112.

To obtain two separate chips, the wafer is cleaved by at least 3*2 cuts. Optionally, the wafer is cleaved by 2 cuts first followed by 3 cuts, as shown in FIG. 5 and FIG. 6, or alternatively the wafer is cleaved by 3 cuts first followed by 2 cuts, as shown in FIG. 5A and FIG. 6. These cuts are either parallel with or perpendicular to the previous one or the later one and a suitable width, such as about 0.8 cm to about 1 cm, is formed by two parallel cuts. These cuts may be carried out by cleaving or dicing.

Figure 7:
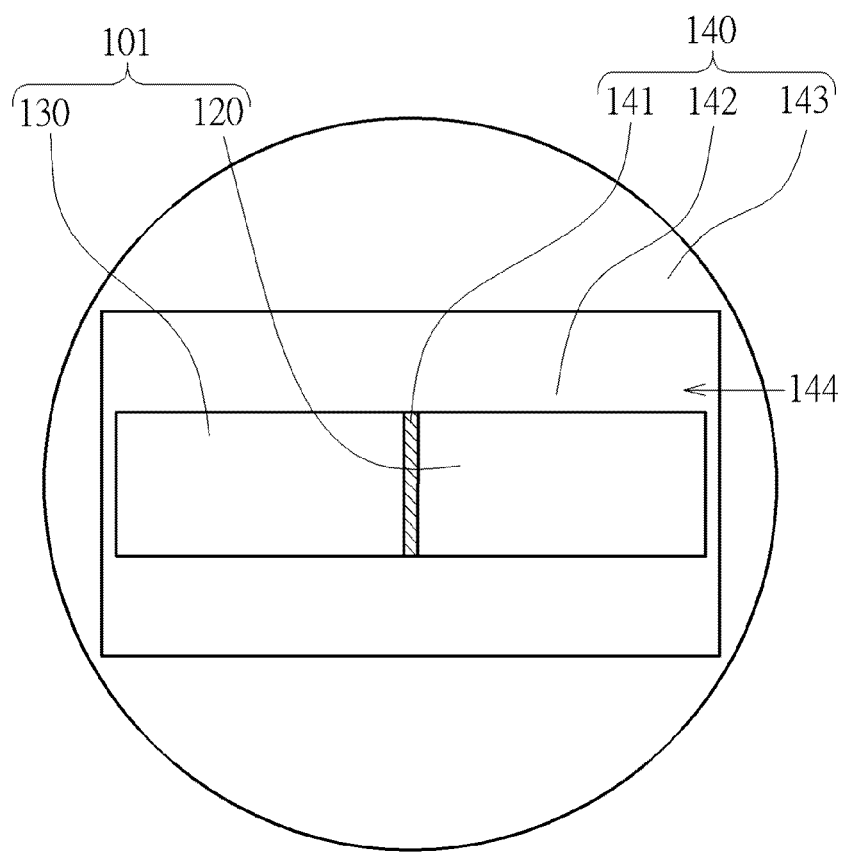
Figure 7A:
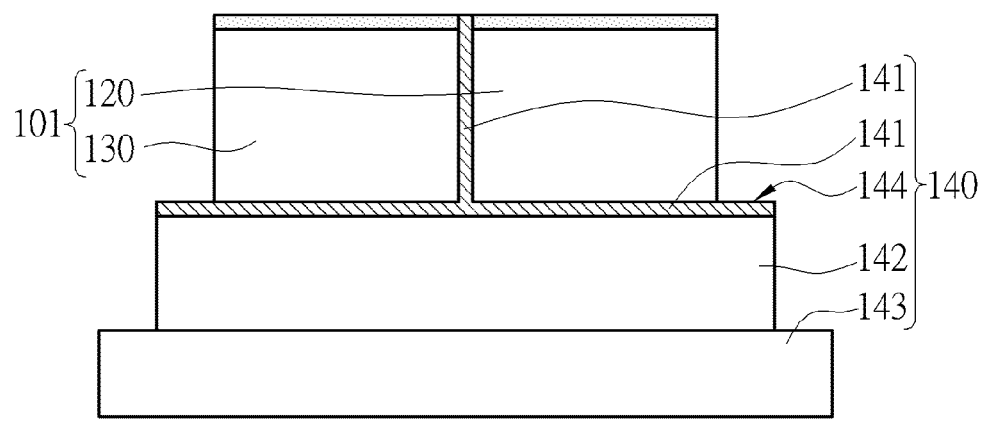

Then, as shown in FIG. 7 and FIG. 7A, the chips 120/130 in the chip set 101 are arranged and fixed on a platform 140 to facilitate the shaping of a TEM sample. FIG. 7 illustrates a top view of the chips in the chip set arranged and fixed on the platform and FIG. 7A illustrates a side view of the chips in the chip set arranged and fixed on the platform.

For example, the platform 140 includes a wax 141, a dummy plate 142 and a tape 143. The wax 141 helps the chip set 101 stick to the top surface 144 of the platform 140 and the wax 141 is easily removed by heat in a later stage. The dummy plate 142 helps support the chip set 101 stick to the wax 141 and the tape 143 helps the platform 140 fixed to a carrier (not shown) in a later stage. The carrier may be an annular frame such as a mounter.

Figure 8:
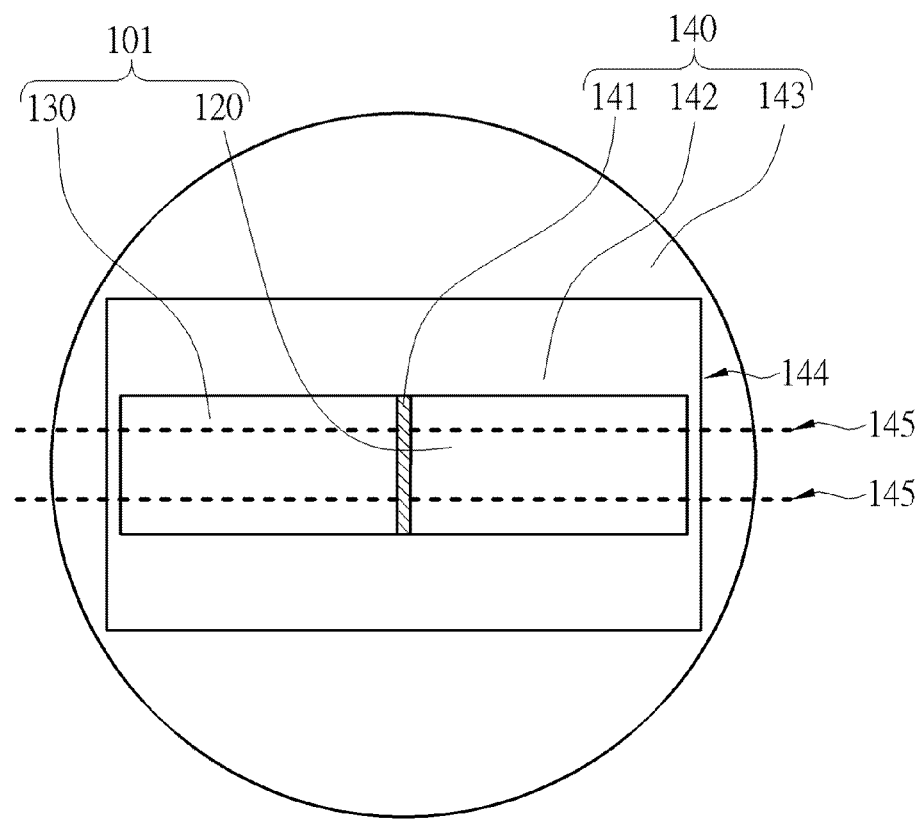
Figure 8A:
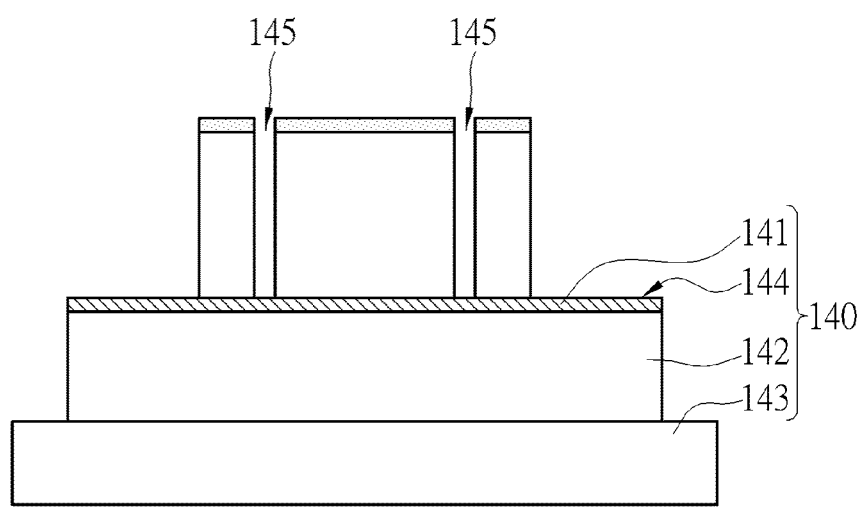

Next, the chips 120/130 in the chip set 101 on the platform 140 are diced and "trimmed" to obtain a specific profile, such as a wine-bottle profile with a pair of shoulders. To dice the chip set 101 may be carried out before or after to trim the chip set 101. For example, as shown in FIG. 8 and FIG. 8A, the chips 120/130 in the chip set 101 are firstly diced across the whole chip set 101 to reduce the dimension perpendicular to the vertical wall of the wax 141. Preferably, the reduced dimension of the chip set 101 after the first dicing 145 may be about 1.2 mm to about 3 mm. FIG. 8 illustrates a top view of the chip set arranged and fixed on the platform and FIG. 8A illustrates a side view of the chip set arranged and fixed on the platform.

Figure 9:
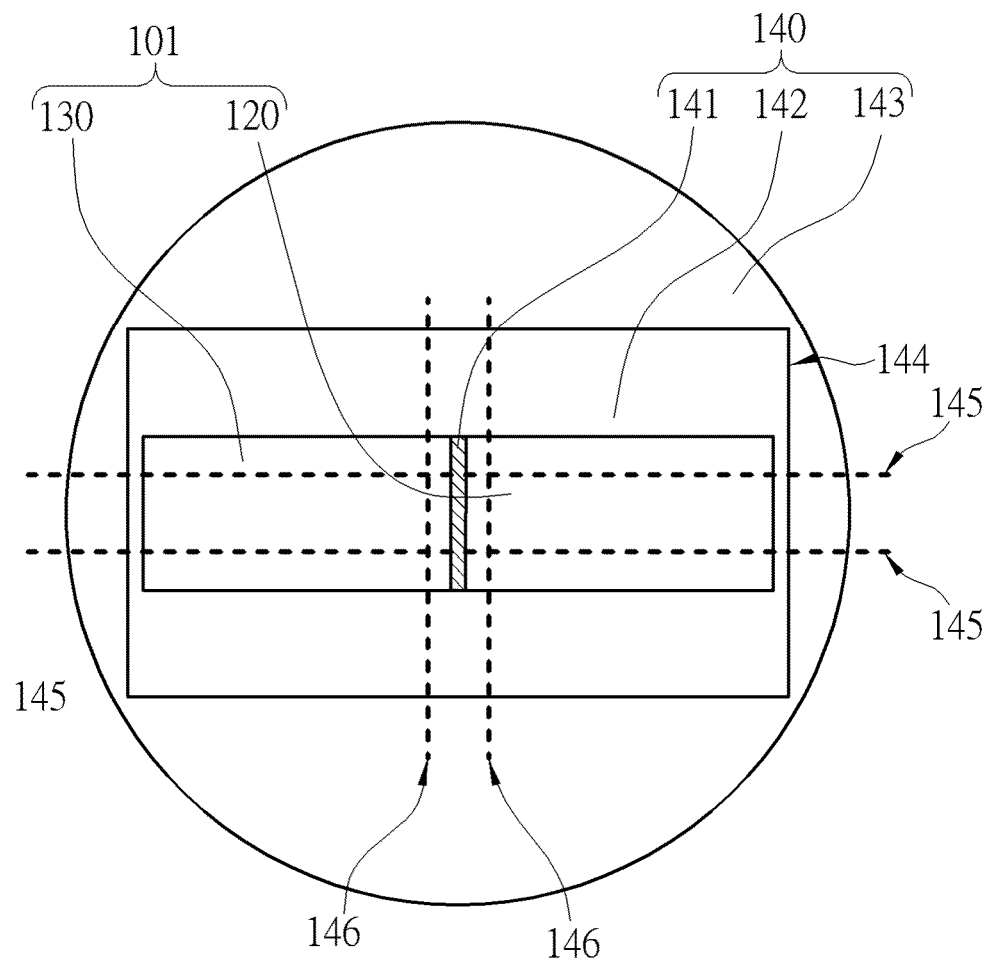

Secondly, as shown in FIG. 9, the chips 120/130 in the chip set 101 are diced again across the whole chip set 101 to reduce the dimension parallel with the vertical wall of the wax 141, usually with the help of a dicing saw. After the second dicing 146, as seen in FIG. 9, another dimension of the chip set 101 are greatly reduced with the help of the platform 140. FIG. 9 illustrates a top view of the chip set arranged and fixed on the platform.

Figure 10:
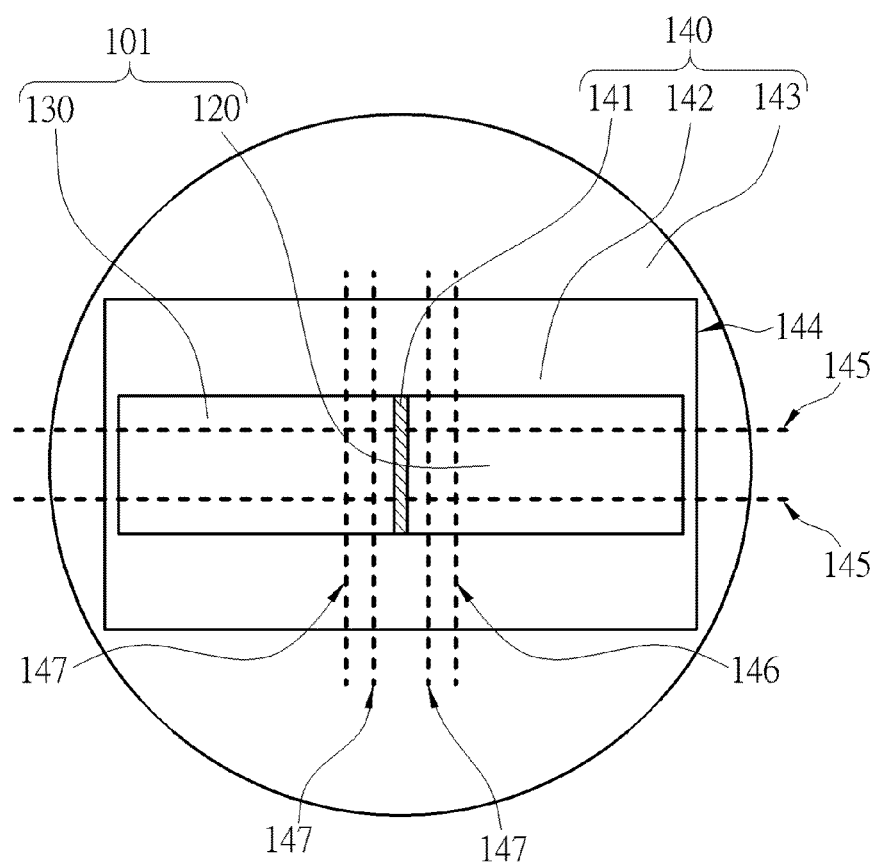
Figure 10A:
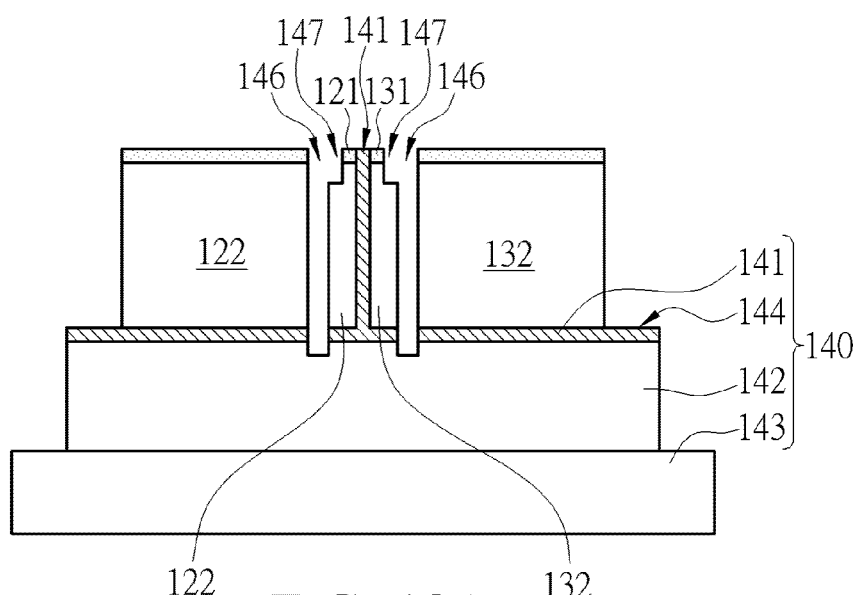

Later, please refer to FIGS. 10 and 10A, still a third dicing 147 is carried out. The third dicing 147 is adjacent to the second dicing 146 and closer to the vertical wall of the wax 141 across the whole chip set 101 to give the chip set 101 a pair of trimmed shoulders 147. All of the above the first dicing 145, the second dicing 146 and the third dicing 147 are carried out in double cuts. However, unlike the first dicing 145 and the second dicing 146, which are deep enough to penetrate the chips 120/130, preferably to reach the wax 141, the top surface 144 or even deeper to the dummy plate 142, the third dicing 147 is preferably a shallower cut.

For example, the third dicing 147 may merely go through the target layer 121/131 to expose the underlying substrate 122/132. Preferably, the third dicing 147 does not expose the underlying wax 141. The reduced dimension by the third dicing 147 may be about 20 µm to about 40 µm. FIG. 10 illustrates a top view of the chip set which is arranged and fixed on the platform and FIG. 10A illustrates a side view of the chip set which is arranged and fixed on the platform.

Figure 11:
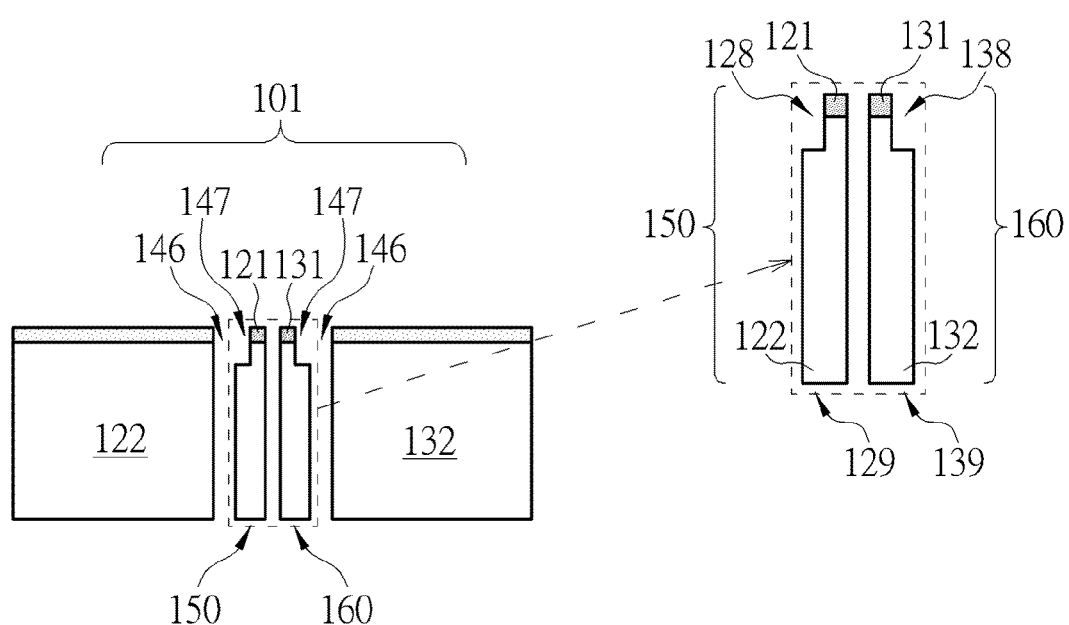

After the above steps, the chip set 101 is cut several times to form a sample dice and a dummy dice. This step is arbitrary so in other words, one of the chips 120/130 may be a sample dice and the other may be a dummy dice. The sample dice and the dummy dice, each has a shoulder portion and a bottom portion. As shown in FIG. 11, after the wax (not shown) is removed by heat, the chip set 101 splits and becomes the sample dice 150 and the dummy dice 160. Shoulder portions 128/138 of the sample dice 150 and the dummy dice 160 have the target layer 121, the target layer 131, the substrate 122 and the substrate 132. Bottom portions 129/139 of the sample dice 150 and of the dummy dice 160 consist of the substrate 122 and the substrate 132. Preferably, the third dicing 147 makes each one of the shoulder portion 128 and the shoulder portion 138 have a dimension from 0 µm to about 20 µm.

Figure 12:
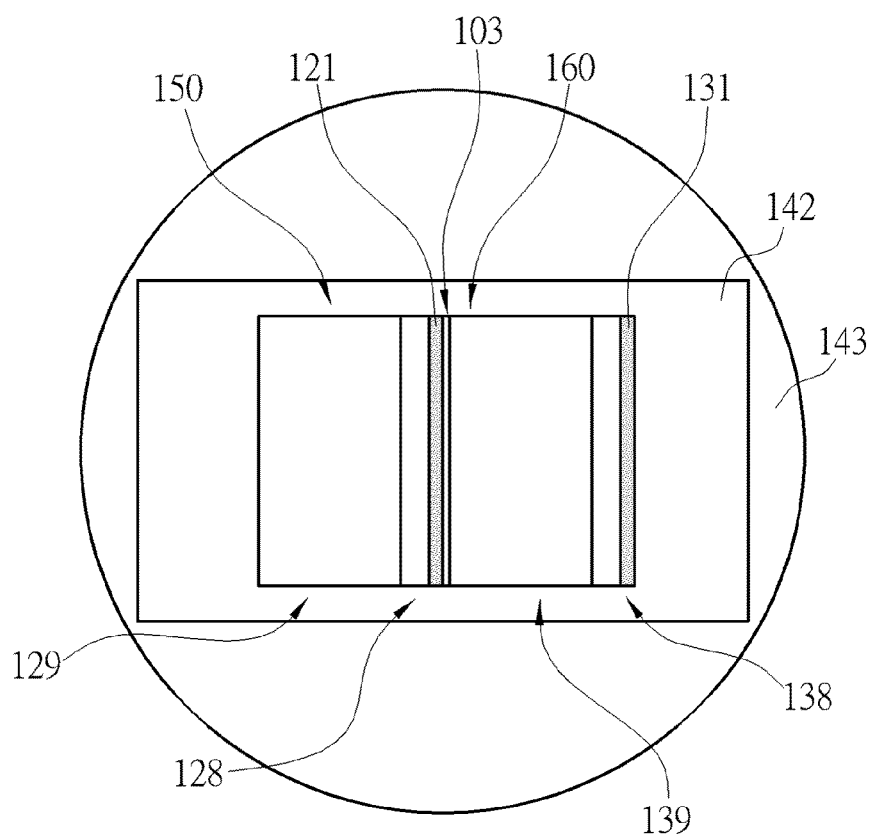
Figure 12A:
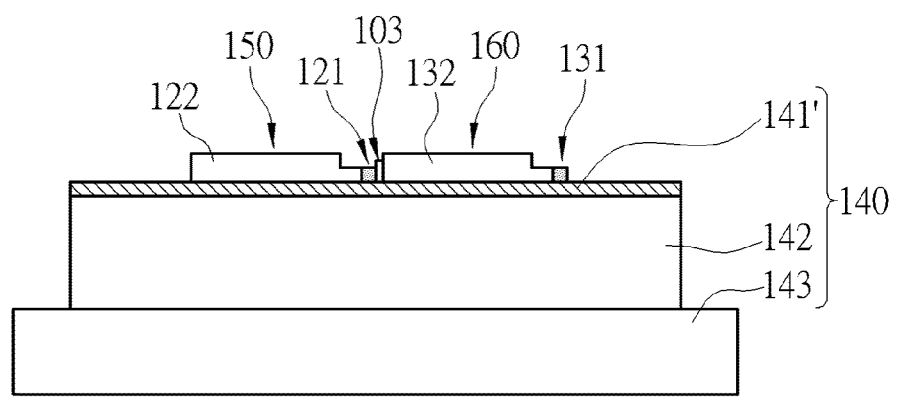

Afterwards, as shown in FIGS. 12 and 12A, the shoulder portion 128 of the sample dice 150 is attached to the bottom portion 139 of the dummy dice 160 by an adhesive 103 in a head-to-tail position on the platform 140 by means another wax 141'. In other words, the target layer 121 of the sample dice 150 is attached to the substrate 132 of the dummy dice 160 by the adhesive layer 103. In one aspect, this arrangement makes the target layer 121 sandwiched between the substrate 122 and the adhesive 103. In another aspect, this arrangement makes the adhesive 103 sandwiched between the target layer 121 and dummy dice 160. The target layer 121 is the sample for the structural analysis and characterization of materials and has composite material layers including a semicinductive material. The adhesive 103 may be an organic material different from the wax 141', for example an epoxy resin. At this stage, other parts of the sample dice 150 become surplus and need removing. FIG. 12 illustrates a top view and FIG. 12A illustrates a side view.

Figure 13:
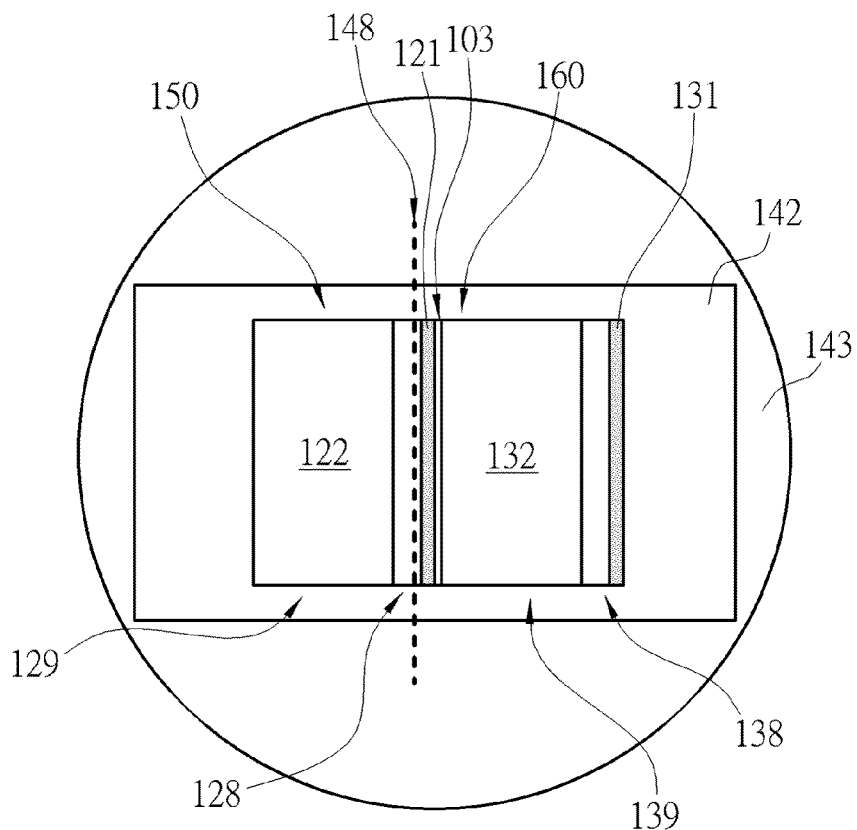
Figure 13A:
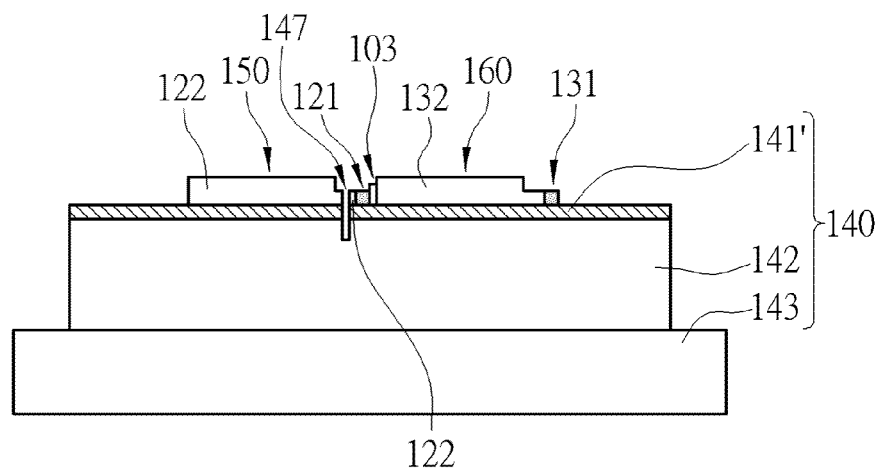

Accordingly, as shown in FIGS. 13 and 13A, a fourth dicing 148 is carried out across the shoulder portion 128 of the sample dice 150 to cut off the substrate 122 along with the bottom portion 128 of the sample dice 150, usually with the help of a dicing saw. FIG. 13 illustrates a top view and FIG. 13A illustrates a side view.

Unlike the previous dicing steps, a single cut is preferably needed in the fourth dicing 148 step. After the fourth dicing 148, the target layer 121 is attached to the bottom portion 139 of the dummy dice 160 by means of the adhesive 103. Optionally, some of the substrate 122 with a proper thickness remains attached to the target layer 121 to protect the target. Usually, the adhesive 103 may be slightly larger than the target layer 121 in terms of the interface.

Figure 14:
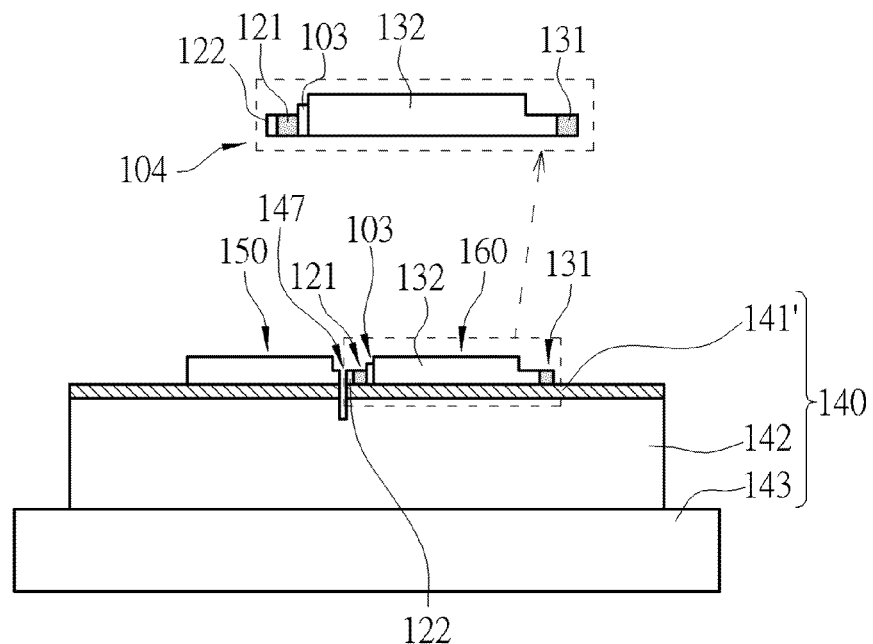
FIG. 14 illustrates the primary sample stack structure of the present invention.

After the previous procedures, a primary sample stack structure 104 with multiple layers is obtained. Please refer to FIG. 14. FIG. 14 illustrates the primary sample stack structure 104 of the present invention. The primary sample stack structure 104 includes a substrate, an adhesive layer 103 and a target layer 121. The substrate may be the substrate 122 or the substrate 132. The target layer 121 has the micro material structures for the structural analysis and characterization of materials by TEM.

The target layer 121 is directly attached to the adhesive layer 103 which is disposed at one end of the substrate 132. The adhesive layer 103 is sandwiched between the substrate 132 and the target layer 121. Optionally, there may be a surplus target layer 131 which is attached to the other end of the substrate 132. The two ends are opposite to each other. Possibly, there may be another substrate 122 which covers the target layer 121 so that the target layer 121 is sandwiched between the substrate 122 and the adhesive layer 103.

Figure 15:
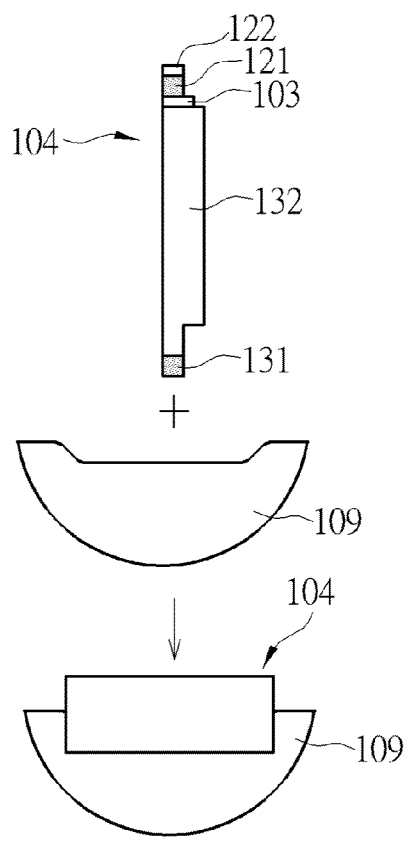
FIG. 15 illustrates the primary sample stack structure is attached to a half copper ring.

This primary sample stack structure 104 is ready to be attached to a base by an epoxy resin to serve as a sample of a TEM. The base may be a half copper ring 109 as show in FIG. 15.

In one preferred embodiment of the present invention, the primary sample stack structure 104 may be further modified, for instance with the help of a focus ion beam system, to facilitate the observation of the TEM. For example, please refer to FIG. 16, part of the sample stack structure 105 may be removed by a focus ion beam system to form a first trench 170. The first trench 170 at least occupies the target layer 121 and the optional substrate 122. The first trench 170 may further occupy the adhesive layer 103 and the substrate 160. The first trench 170 may have a width W1 from about 25 µm to about 60 µm. The smallest dimension L of the topmost surface of the primary sample stack structure 105 may be about 500 Å to about 4000 Å.

Figure 16:
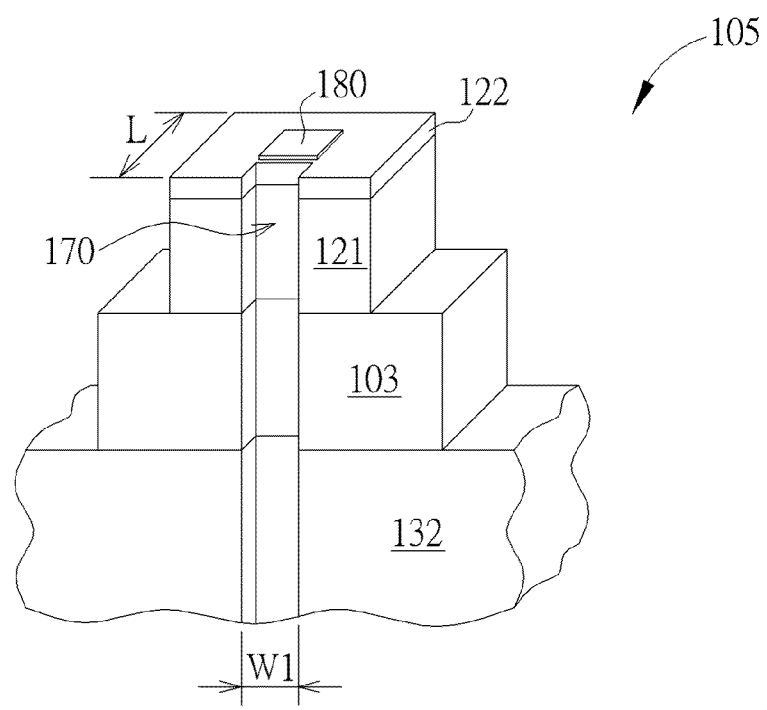
FIG. 16 illustrates part of the sample stack structure is removed to form a first trench.

In another preferred embodiment of the present invention, as shown in FIG. 16, a metal pad 180 may be formed on the topmost surface of the primary sample stack structure 105, for example on the target layer 121 or on the optional substrate 122. For example, the metal pad 180 may include Pt and measure about 6 µm*1 µm*1 µm. The metal pad 180 serves as a protection layer, such as a layer of Pt, C or W, to keep underneath structures from focus ion beam damage during the ion milling. The metal pad 180 may be formed by using a FIB system to deposit the protection layer with a size ranging from about 5 µm*1 µm*1 µm to about 10 µm*2 µm*2 µm. In the presence of the metal pad 180, the bottom of the first trench 170 may be as close to the metal pad 180 as possible but the bottom of the first trench 170 is not in direct contact with the metal pad 180.

Figure 17:
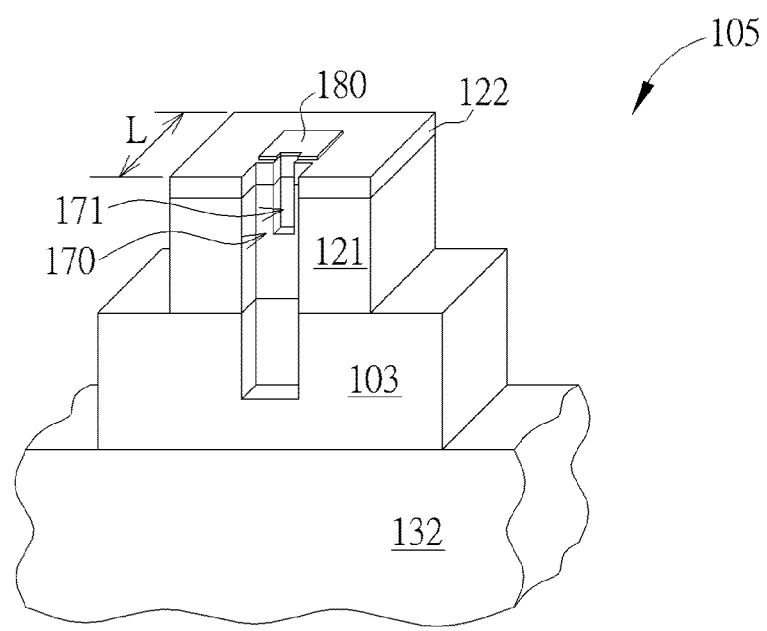
FIG. 17 illustrates part of the sample stack structure is removed to form a first via.

In another embodiment of the present invention, as shown in FIG. 17, a first via 171 may be form to connect the first trench 170. Like the first trench 170, the first via 171 also at least occupies the target layer 121 and the optional substrate 122 and may further occupy the adhesive layer 103 and the substrate 160. But unlike the first trench 170, the formation of the first via 171 removes some of the metal pad 180.

Figure 18:
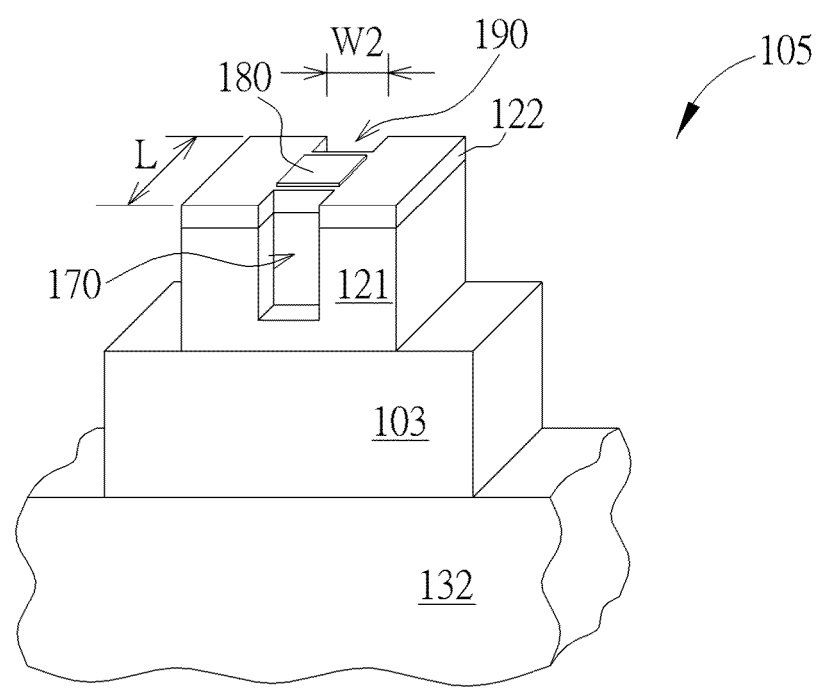
FIG. 18 illustrates part of the sample stack structure is removed to form a second trench.

In another embodiment of the present invention, the sample stack structure 105 may possibly have a second trench 190. Please refer to FIG. 18, part of the sample stack structure 104 are removed to form the second trench 190. Like the first trench 170, the second trench 190 at least occupies the target layer 121 and the optional substrate 122, or may further occupy the adhesive layer 103 and the substrate 160. The bottom of the second trench 190 may be as close to the metal pad 180 as possible but is not in direct contact with the metal pad 180. The second trench 190 may have a width W2 from about 25 µm to about 60 µm). In particular, the second trench 190 and the first trench 170 are disposed at two opposite sides of the sample stack structure 105.

Figure 19:
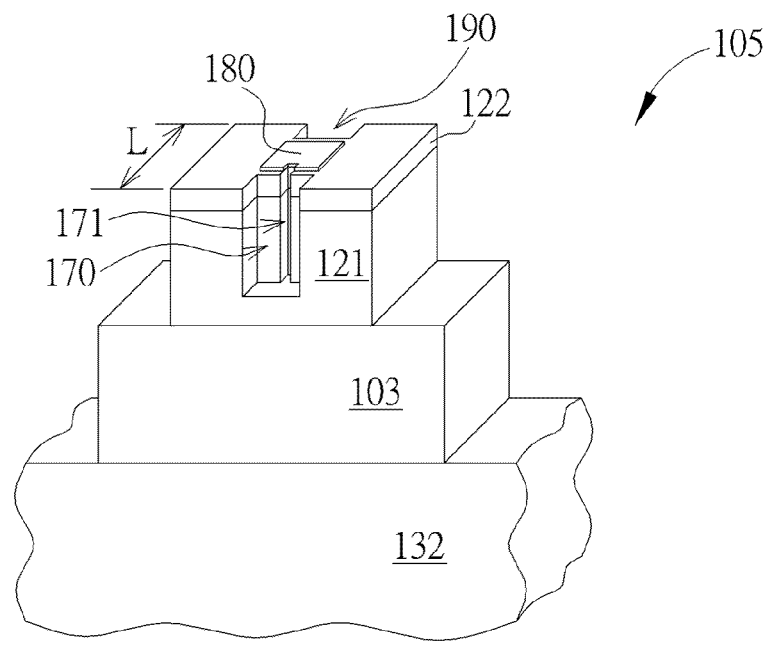
FIG. 19 and FIG. 19A illustrate part of the sample stack structure is removed to form a second via.
Figure 19A:
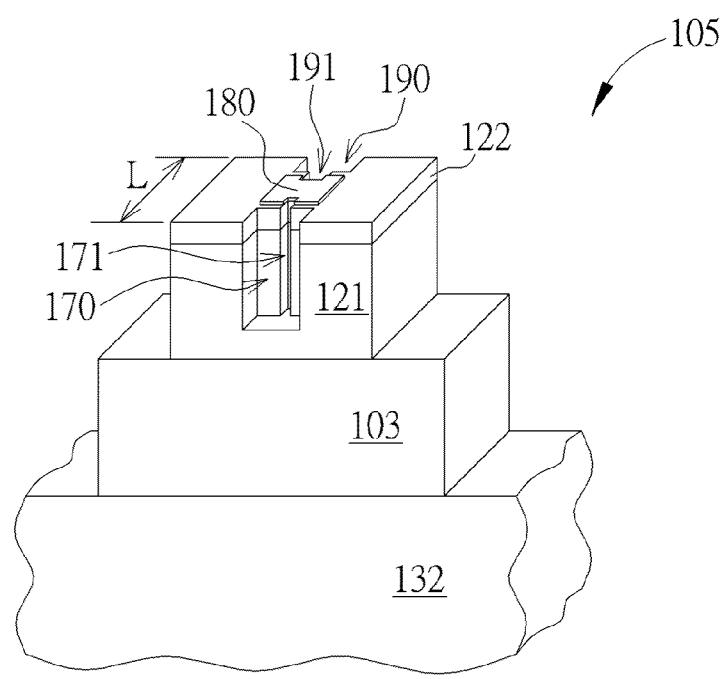

In still another embodiment of the present invention, the sample stack structure 105 may optionally have a second via 191 which connects the second trench 190, as shown in FIG. 19 and FIG. 19A. Like the second trench 190, the second via 191 also at least occupies the target layer 121 and the optional substrate 122 and may further occupy the adhesive layer 103 and the substrate 160. The formation of the second via 191 removes some of the metal pad 180, like the first via 171. The first trench 170, the first via 171, the second trench 190 and the second via 191 may be formed in a similar way. Preferably, the second trench 190 is independent of the first trench 170, and the second via 191 is independent of the first via 171. The purpose of the trenches 170/190 and the vias 171/191 is to form a foil with a thickness ranging from about 15 nm to about 0.4 µm for TEM analysis. Generally, these are formed in the following sequence: the trench 170, the trench 190, the via 171 and then the via 191.

Figure 20A:
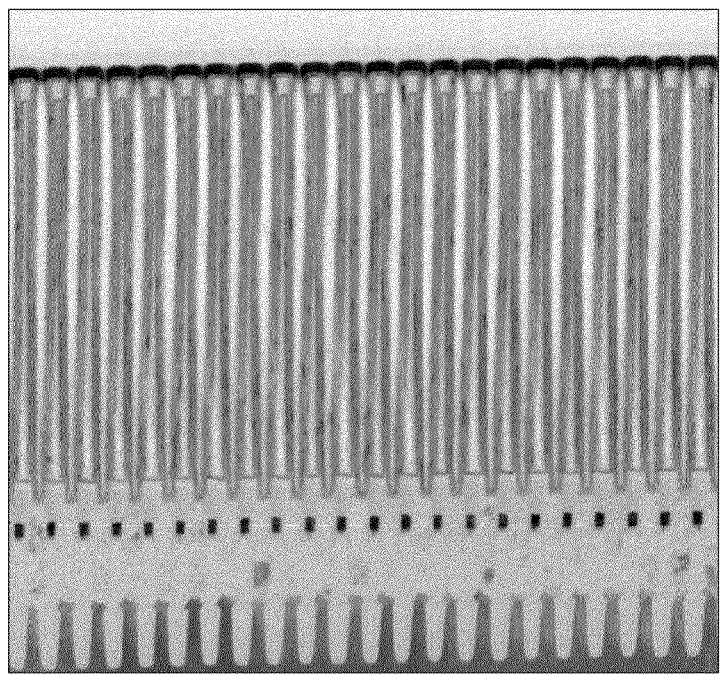
FIG. 20A, FIG. 20B and FIG. 20C each shows an example of the TEM sample with no substantial curtain effect by using the method of the present invention.
Figure 20B:
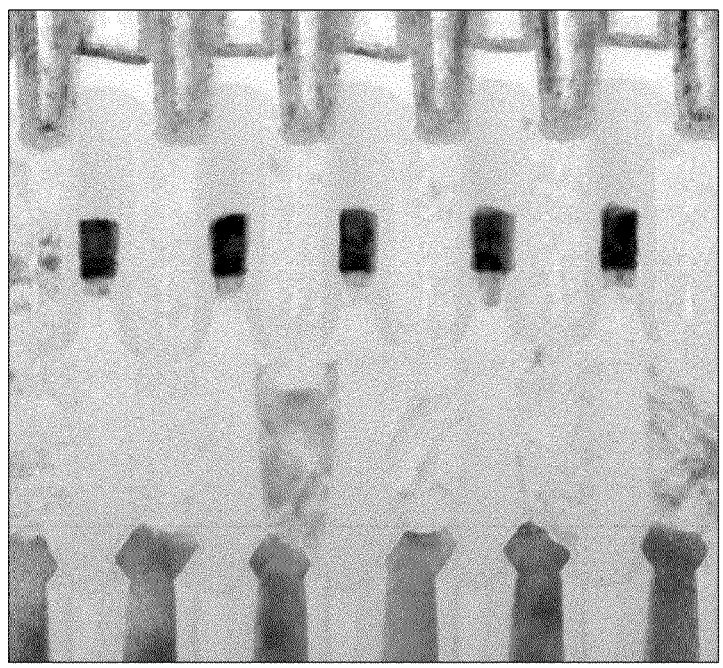
Figure 20C:
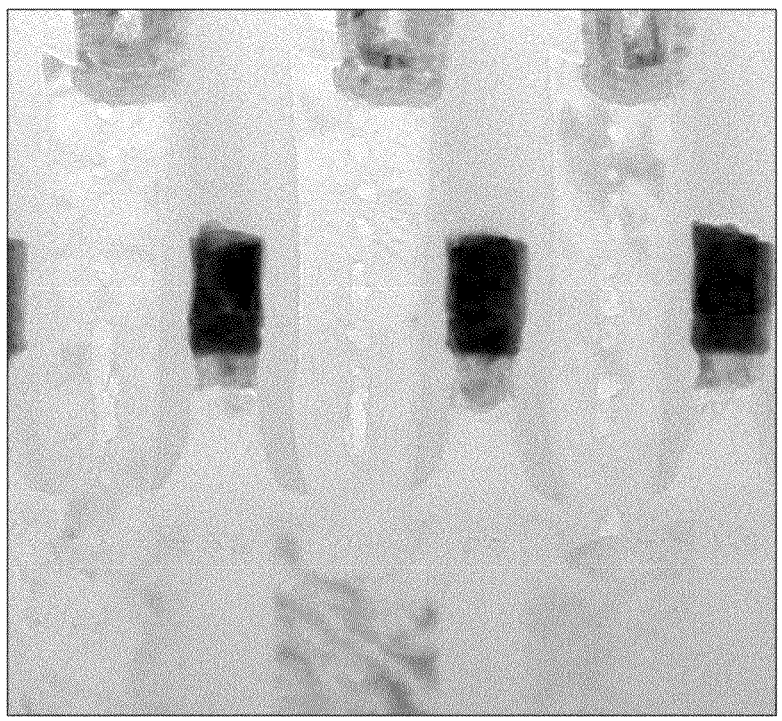

FIG. 20A, FIG. 20B and FIG. 20C show examples of the primary sample stack structure 104 or the sample stack structure 105 with no curtain effect by using the method of the present invention.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for preparing a sample stack structure, comprising:
   providing a chip set comprising at least two dices and each chip comprising a substrate and a target layer;
   cutting said chip set at least four times to form a sample dice and a dummy dice and each said sample dice and said dummy dice has a shoulder portion and a bottom portion, wherein said shoulder portion has said substrate and said target layer;
   attaching said target layer of said sample dice to said substrate of said dummy dice by an adhesive layer; and
   removing said bottom portion of said sample dice so that said target layer and some of said substrate of said sample dice are attached to said dummy dice by said adhesive layer to obtain a sample stack structure.

2. The method for preparing a sample stack structure of claim 1, wherein said chip set comprises a first dice and a second dice so that said first dice is said sample dice and said second dice is said dummy dice.

3. The method for preparing a sample stack structure of claim 1, wherein said adhesive layer comprises an epoxy resin.

4. The method for preparing a sample stack structure of claim 1, wherein said target layer comprises a composite material comprising a semiconductive material.

5. The method for preparing a sample stack structure of claim 1, wherein said shoulder portion of said sample dice is attached to said bottom portion of said dummy dice by said adhesive layer.

6. The method for preparing a sample stack structure of claim 1, further comprising:
   forming a metal pad on said substrate of said sample dice after removing said bottom portion of said sample dice.

7. The method for preparing a sample stack structure of claim 1, further comprising:
   forming a first trench occupying said target layer.

8. The method for preparing a sample stack structure of claim 7, further comprising:
   forming a first via connecting said first trench and occupying said target layer.

9. The method for preparing a sample stack structure of claim 7, further comprising:
   forming a second trench occupying said target layer, wherein said second trench and said first trench are disposed on two opposite sides of said sample dice.

10. The method for preparing a sample stack structure of claim 9, further comprising:
    forming a second via connecting said second trench and occupying said target layer.

* * * * *